US007135101B2

(12) United States Patent
Atchison et al.

(10) Patent No.: US 7,135,101 B2
(45) Date of Patent: Nov. 14, 2006

(54) CASSETTE ASSEMBLY FOR ELECTROPHORESIS GELS

(75) Inventors: Shaun Atchison, Killarney Heights (AU); Jens Sommer-Knudsen, St. Ives (AU); Nicola Boyd, Holgate (AU); Des Berry, Mt. Eliza (AU)

(73) Assignee: Life Therapeutics, Frenchs Forest NSW (AU)

( * ) Notice: Subject to any disclaimer, the term of this patent is extended or adjusted under 35 U.S.C. 154(b) by 0 days.

(21) Appl. No.: 10/000,473

(22) Filed: Oct. 24, 2001

(65) Prior Publication Data

US 2002/0070115 A1 Jun. 13, 2002

(30) Foreign Application Priority Data

Oct. 26, 2000 (AU) .................................. PR1036

(51) Int. Cl.
*G01N 27/447* (2006.01)
*G01N 27/453* (2006.01)
(52) U.S. Cl. ........................ 204/467; 204/618
(58) Field of Classification Search ................ 204/456, 204/465, 470, 606, 615, 619, 620, 466, 467, 204/616, 618
See application file for complete search history.

(56) References Cited

U.S. PATENT DOCUMENTS 4,919,784 A * 4/1990 Yetman ...................... 204/612
5,228,465 A * 7/1993 Hill ............................. 132/212
5,569,369 A 10/1996 Leffler et al.
5,938,906 A 8/1999 Moi et al.
6,436,262 B1 * 8/2002 Perez ........................ 204/618

FOREIGN PATENT DOCUMENTS

WO WO 97/04307 2/1997
WO WO 98/16820 4/1998

* cited by examiner

*Primary Examiner*—Kaj K. Olsen
(74) *Attorney, Agent, or Firm*—Cooley Godward LLP (57) ABSTRACT

This invention is directed to a cassette for electrophoresis gels comprising: first and second planar wall members having inner and outer surfaces, top and bottom edges, and lateral edges wherein the wall members are oriented generally parallel to each other and such that the inner wall of each wall member is proximate to the inner wall of the other wall member; spacing means disposed between the inner walls of the wall members and adapted to provide a space for an electrophoresis gel between the inner walls of the wall members, wherein the cassette has an interior which is defined by the space between the wall members; and locking means adapted to prevent locking engagement of the members unless the inner surfaces of the wall members and are substantially parallel to each other and are separated by a predetermined distance, and when the wall members are in locked engagement, to substantially prevent any movement of the wall members away from such locked engagement.

26 Claims, 11 Drawing Sheets

CASSETTE ASSEMBLY FOR ELECTROPHORESIS GELS

BACKGROUND OF THE INVENTION

The present invention relates to a cassette for use in the formation of an electrophoretic gel. More particularly, the invention relates to such cassettes made of two parts and having locking means for holding the two parts together in a desired orientation. The subject invention also relates to a method for separating analytes, such as bio-organic molecules by the use of the above-mentioned cassettes.

Electrophoresis is the resolution of a complex mixture of macromolecules on the basis of charge and/or size under the influence of an electric field. Usually, separation of the charged molecules is based on the strength of the electrical field and the net charge, size and shape of the molecules. The separation can also, at least in part, be affected by other parameters, such as isoelectric points, ionic strength, viscosity and temperature of the medium in which the charged molecules are moving. As proteins and other biological molecules, such as DNA, RNA, enzymes, carbohydrates and the like are charged, electrophoresis techniques are ideal to separate them for analytical or preparative purposes.

It is common practice to use a cassette for conducting gel electrophoresis. The cassette comprises two flat plates, usually transparent glass or plastic, separated by spacing means and sealed along the sides and bottom edges to provide a void or confined space between the plates for placement of a suitable separation gel medium or electrophoresis gel such as agarose or a polyacrylamide in liquid form and its subsequent gelling or polymerization. The bottom of the cassette may be sealed with tape, another spacer, or by compression against a gasket. Once sealed on the edges and bottom, a solution of acrylamide, polymerization catalysts and buffers are introduced into the cassette and allowed to polymerize. After the gel has formed, the seal on the bottom, if used, is removed to provide an electrical contact for electrophoresis.

Automating this casting procedure is a means of reducing cost, user labor, and improving reproducibility. When a separation is run on the gel in the cassette, the top portion of the gel is in contact with a buffered solution and the lower portion of the gel is in contact with a second buffered solution. An electric current is applied to the buffered solution(s) or the gel, causing the migration and separation of the samples. By convention, the samples, for example, negatively charged proteins and nucleic acids, tend to run from the cathode (the top of the cassette, where the sample is placed) to the anode of the gel.

For the purposes of describing this invention, reference to the top or upper end of a cassette means the end of the cassette at which the wells are formed and in the instance of negatively charged samples, the cathode end of the gel. Additionally, the use of the terms "gelled" and "gel" refers to a solid state of the electrophoretic medium whether it be due to the cooling of an agarose gel or the polymerization of an acrylamide or acrylamide derivative.

In protein or nucleic acid fragment analysis, it is desirable to run more than one sample in a gel and to keep the samples separate. This is accomplished by sample separating means which is most commonly provided by the formation of wells at the sample-loading end of the gel (ie near the upper end of the cassette). Sample wells are formed usually by means of a removable piece or "comb" with teeth having the desired shape of the wells and having straight (level) substantially perpendicular ends to the teeth. The comb is brought into contact with the liquid separation medium before it gels or polymerizes and is positioned so that the teeth extend into the liquid medium while it gels. After the gel has set, the comb is removed to leave wells where samples can be positioned.

To improve the separation of certain types of molecules, it is common practice to change the composition of the gel medium in the direction of the electrophoresis. This change in composition can, for example, take the form of a discontinuity formed by a stacking gel at the upper most portion of the gel and a resolving gel at the lower most portion of the gel. Another example of a change in composition is the commonly used gradient gel consisting of a continuous gradient or a discreet gradient of bands each of uniform but different composition or any combination of continuous and discreet gradient. In order to provide accurate sample resolution, it is necessary that the desired electrophoresis composition remain undisturbed until the gel medium has gelled or polymerized completely, particularly in the instance of stacking and/or gradient gels.

Additionally, the uniformity of the gel is important to the quality of the separation obtained, for example, uniformity in the porosity of the gel or regions of the gel, uniformity (level and perpendicular to the plates) in the edge of the gel which first contacts the samples, uniformity in the thickness of the gel and uniformity (level and perpendicular to the plates) in the interface between discreet bands of gels (for example, between gradient gels or between stacking and resolving gels). Thus, it is desirable that the liquid gel-forming medium introduced into the cassette be disturbed as little as possible while gelling.

Casting polyacrylamide gels for vertical electrophoresis is commonly done by creating a cassette formed of two glass or plastic parallel sheets. Typically, the parallel sheets are held in position by a pair of spacers located at the vertical edges of the sheets. These spacers typically perform the functions of connecting the parallel sheets and keeping the faces of the sheets apart, creating a cavity for receiving the electrophoretic gel. The spacers also serve to maintain the sheets in substantially parallel orientation. The connection between the parallel sheets is sometimes effected by the use of corresponding ridges and recesses which form a friction-fit or snap-fit. This means of connecting the parallel sheets has been found to be inadequate. For instance, the connection may not be entirely even along the lengths of the spacers and small gaps may exist at points between the corresponding ridges and recesses. These gaps can cause slight variations in the distance between the parallel sheets. The gaps can also cause leakage of the gel to occur. Another problem with this means of connecting the parallel sheets is that there is nothing to prevent the sheets from undergoing some movement relative to one another. For instance, if the cassette is inadvertently knocked or bumped (perhaps during transportation), the connection between the sheets may be loosened and they may separate slightly from one another. In this case, the space between sheets may not be entirely uniform throughout.

In order to inhibit leakage and to enhance the connection between the sheets, the spacers of one wall member are sometimes glued or welded to the other wall member. However, the use of glue or welding is still not sufficient to ensure that the faces of the parallel sheets are in fact completely parallel over their entire areas. This is often because the spacers may not correctly engage the opposite wall member at all points along the spacers. For instance, small gaps may still exist at some points. Similarly, the use of glue or welding may cause slight inconsistencies resulting in non-uniform engagement between the spacers and the opposite wall members. When the opposed wall members are not completely parallel, the electrophoretic gel will not be of uniform thickness. The nearer the gel can be to having uniform thickness throughout, the better and more reliable will be the results of the electrophoretic procedure.

Accordingly, the present invention is directed towards a cassette for holding an electrophoretic gel having improved uniformity of thickness of the gel.

SUMMARY OF THE INVENTION

In accordance with the present invention, there is provided a cassette for holding an electrophoretic gel having improved uniformity of thickness of the gel.

Further, in accordance with the present invention, there is provided a cassette which allows the user to use the cassette immediately and with much greater convenience than compared to existing pre-cast gels.

Still further, in accordance with the present invention there is provided a cassette for electrophoresis gels comprising:
 a first planar wall member having inner and outer surfaces, top and bottom edges, and lateral edges;
 a second planar wall member having inner and outer surfaces, top and back edges, and lateral edges, wherein the first and second wall members are oriented generally parallel to each other and such that the inner wall of the first wall member is proximate to the inner wall of the second wall member;
 spacing means disposed between the inner walls of the first and second wall members and adapted to provide a space for an electrophoresis gel between the inner walls of the first and second wall members, wherein the cassette has an interior which is defined by the space between the first wall member and the second wall member; and
 locking means adapted to prevent locking engagement of the first and second wall members unless the inner surface of the first wall member and the inner surface of the second wall member are substantially parallel to each other and are separated by a predetermined distance and, when the first and second wall members are in locked engagement, to substantially prevent any movement of the wall members away from such locked engagement.

Still further, in accordance with the present invention, there is provided a cassette for electrophoresis gels comprising:
 a first planar wall member having inner and outer surfaces, top and bottom edges, and lateral edges;
 a second planar wall member having inner and outer surfaces, top and back edges, and lateral edges, wherein the first and second wall members are oriented generally parallel to each other and such that the inner wall of the first wall member is proximate to the inner wall of the second wall member;
 spacing means disposed between the inner walls of the first and second wall members and adapted to provide a space for an electrophoresis gel between the inner walls of the first and second wall members, wherein the cassette has an interior which is defined by the space between the first wall member and the second wall member;
 locking means adapted to prevent locking engagement of the first and second wall members unless the inner surface of the first wall member and the inner surface of the second wall member are substantially parallel to each other and are separated by a predetermined distance and, when the first and second wall members are in locked engagement, to substantially prevent any movement of the wall members away from such locked engagement;
 positioning means adapted to position a removable buffer chamber on the upper end of the cassette; and
 a removable buffer chamber adapted to be positioned on the upper end of the cassette.

Still further in accordance with the present invention, there is provided a cassette for electrophoresis gels comprising:
 a first planar wall member having inner and outer surfaces, top and bottom edges, and lateral edges;
 a second planar wall member having inner and outer surfaces, top and back edges, and lateral edges, wherein the first and second wall members are oriented generally parallel to each other and such that the inner wall of the first wall member is proximate to the inner wall of the second wall member;
 spacing means disposed between the inner walls of the first and second wall members and adapted to provide a space for an electrophoresis gel between the inner walls of the first and second wall members, wherein the cassette has an interior which is defined by the space between the first wall member and the second wall member;
 locking means adapted to prevent locking engagement of the first and second wall members unless the inner surface of the first wall member and the inner surface of the second wall member are substantially parallel to each other and are separated by a predetermined distance and, when the first and second wall members are in locked engagement, to substantially prevent any movement of the wall members away from such locked engagement;
 an electrophoresis gel material within the interior of the cassette, wherein the gel comprises at least two gel fingers, separated from each other, and located proximate to the upper end of the gel,
 at least two wells located above the at least two gel fingers, wherein one of the wells is larger than the other well; and
 a removable plug located in the smaller of the wells.

Still further, in accordance with the present invention, there is provided a method of preparing a pre-cast electrophoresis gel comprising:
 inserting at least one spacer into the top of a cassette for electrophoresis gels, the cassette comprising a first planar wall member having inner and outer surfaces, top and bottom edges, and lateral edges; a second planar wall member having inner and outer surfaces, top and back edges, and lateral edges, wherein the first and second wall members are oriented generally parallel to each other and such that the inner wall of the first wall member is proximate to the inner wall of the second wall member; spacing means disposed between the inner walls of the first and second wall members and adapted to provide a space for an electrophoresis gel between the inner walls of the first and second wall members, wherein the cassette has an interior which is defined by the space between the first wall member and the second wall member; and locking means adapted to prevent locking engagement of the first and second wall members unless the inner surface of the first wall member and the inner surface of the second wall member are substantially parallel to each other and are separated by a predetermined distance and, when the first and second wall members are in locked engagement, to substantially prevent any movement of the wall members away from such locked engagement;

providing a gel-forming material into the interior of the cassette;

allowing the gel-forming material to form a gel within the interior of the cassette; and removing the spacer from the cassette.

Still further in accordance with the present invention, there is provided a method of preparing a pre-cast electrophoresis gel comprising:

inserting at least one spacer into the top of a cassette for electrophoresis gels, the cassette comprising a first planar wall member having inner and outer surfaces, top and bottom edges, and lateral edges; a second planar wall member having inner and outer surfaces, top and back edges, and lateral edges, wherein the first and second wall members are oriented generally parallel to each other and such that the inner wall of the first wall member is proximate to the inner wall of the second wall member; spacing means disposed between the inner walls of the first and second wall members and adapted to provide a space for an electrophoresis gel between the inner walls of the first and second wall members, wherein the cassette has an interior which is defined by the space between the first wall member and the second wall member; and locking means adapted to prevent locking engagement of the first and second wall members unless the inner surface of the first wall member and the inner surface of the second wall member are substantially parallel to each other and are separated by a predetermined distance and, when the first and second wall members are in locked engagement, to substantially prevent any movement of the wall members away from such locked engagement, wherein the spacer comprises a protrusion projecting from the side of the spacer proximate the interior of the cassette, wherein such protrusion defines two wells within the interior of the cassette, and wherein one of the wells is larger than the other well;

providing a gel-forming material into the interior of the cassette;

allowing the gel-forming material to form a gel within the interior of the cassette;

removing the spacer from the cassette; and inserting a removable plug in the smaller well.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood, preferred forms will be described with reference to the following drawings and examples.

DETAILED DESCRIPTION OF THE INVENTION

Described generally, the invention is directed to a cassette for an electrophoretic gel wherein the cassette comprises a first planar wall member having inner and outer surfaces, top and bottom edges, and lateral edges and a second planar wall member having inner and outer surfaces, top and back edges, and lateral edges, wherein the first and second wall members are oriented generally parallel to each other and such that the inner wall of the first wall member is proximate to the inner wall of the second wall member. The cassette further comprises spacing means disposed between the inner walls of the first and second wall members and adapted to provide a space for an electrophoresis gel between the inner walls of the first and second wall members, wherein the cassette has an interior which is defined by the space between the first wall member and the second wall member. In addition, the cassette comprises locking means adapted to prevent locking engagement of the first and second wall members unless the inner surface of the first wall member and the inner surface of the second wall member are substantially parallel to each other and are separated by a predetermined distance and, when the first and second wall members are in locked engagement, to substantially prevent any movement of the wall members away from such locked engagement. The spacer means preferably includes one or more primary spacing elements located on an inner face of at least one wall member. Preferably, the spacer means includes at least one primary spacing element located adjacent each lateral edge of the wall member. Preferably, the spacing means comprise a plurality of ridges on the inner surface of the first wall member spaced apart from each other, located proximate to each of the lateral edges and extending upwardly from the inner surface, and a plurality of ridges on the inner surface of the second wall member spaced apart from each other, located proximate to each of the lateral sides and extending upwardly from the inner surface, wherein the ridges extending from each lateral edge of the inner surface of the first wall member are adapted to fit within a corresponding space between the ridges extending from each corresponding lateral edge of the inner surface of the second wall member to align and interconnect the first wall member with the second wall member in such a manner that the inner surface of the first wall member and the inner surface of the second wall member are generally parallel to each other. Such ridges (or other similar arrangements) not only separate the opposed inner faces of the opposed wall members by the predetermined distance, but also help to align the two wall members in the desired orientation. The ridges suitably have both horizontal and vertical components. The vertical ridges help place the opposed wall members in horizontal alignment and the horizontal ridges and channels assist with vertical alignment of the wall members.

Preferably, the primary spacing elements are adapted to effect closure of the lateral sides of the gel-receiving space. This is suitably effected by having the primary spacing elements consist of co-operating ridges extending along substantially the entire length of the wall members adjacent said lateral edges.

The spacer means suitably further include one or more secondary spacing elements located intermediate the lateral edges. The secondary spacing element(s) help to maintain the predetermined distance between the opposed inner faces and is (or are) preferably located at one or more positions remote from the lateral edges. However, it is preferred that any secondary spacing elements be located in positions where they will have little or no effect on the electrophoretic process, such as being positioned near the upper end of the gel-receiving space. Preferably, the secondary spacing element suitably consists of a boss (or knob) on one inner face and a complementary mouth on the opposed inner face adapted to receive the boss (or knob). The boss (or knob) and the complementary mouth may be adapted to engage in a snap-fit arrangement.

The locking means is dimensioned so as to enable the two wall members to be locked together only when they are in their predetermined optimum position which, typically, is when the opposed inner faces of the two wall members are parallel. The locking means will not enable locked engagement of the wall members if they are not in this predetermined optimum position. When the two wall members are in locked engagement, the locking means prevents any movement of the wall members away from their predetermined optimum position.

The locking means is preferably located on or adjacent to the lateral edges of the wall members. This location makes it easier to manipulate the locking means when attempting to effect locked engagement between the wall members.

Preferably, the locking means includes at least one male member projecting from each side of one of the wall members, and at least one complementary female member adjacent to each side of the other wall member adapted to receive said male member(s). The locked engagement is preferably effected by a snap-fit between the male and female members. Alternatively, the locking means suitably include an L-shaped member projecting from at or near each lateral edge of one of the wall members adapted so that a portion of it clamps over a complementary ridge or surface of the other wall member. When in locked engagement, the two wall members will not be able to be readily separated from one another. In order to separate the wall members, the locking means will need to be unlocked, for instance by breaking the locking means or otherwise manipulating it.

The locking means is integrally formed as an integral part of at least one of the wall members. Accordingly, it is preferable that the cassette be made of a plastic material which is suitable for electrophoretic procedures. The plastic material is preferably substantially rigid but having a degree of resilience for facilitating the snap-fit or clamping of the locking means.

Preferably, the inner face of one of the wall members includes one or more short longitudinal ribs adjacent an upper end of the wall member. When there are more than one of the ribs, they are positioned in parallel orientation. These short ribs are adapted so that, when the first and second wall members are engaged, the short ribs define a plurality of parallel channels suitable for receiving a well-forming comb or spacer.

These short ribs are suitably adapted so as to extend fully between the opposed inner faces of the first and second wall members when the members are in locked engagement. It is preferred, however, that these short ribs are adapted so as not to extend fully between said inner faces when in locked engagement such that the ends of the ribs to not touch the inner face of the opposed wall member. This enables the electrophoretic gel to enter the small space between the ends of the ribs and the opposed inner face. Thus, in the region of the ribs, a channeled gel-receiving cavity is formed. This arrangement allows for spaced-apart fingers of gel to be formed in the gel-receiving cavity (when the gel is added)

with each finger being joined to an adjoining finger by a thin film of gel (between the end of each rib and the opposed inner face).

It is generally preferred that the plurality of short ribs are spaced apart so as to define channels of substantially equivalent width. Any desired number of short ribs may be included, depending upon the user's requirements. Preferably, there will be between one and about 40 short ribs in any one cassette.

In one preferred form, when the cassette is assembled and filled with gel, gel fingers are formed within the channeled gel-receiving cavity of the ribs and the ribs assist in forming sample-receiving wells in the top of the gel.

Preferably, assembly of the cassette does not require additional welding or gluing of the wall members.

Figure 1:
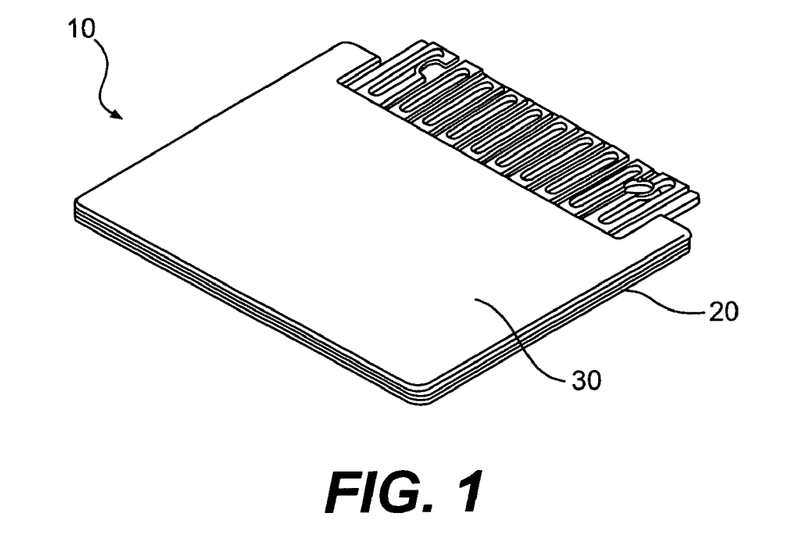
FIG. 1 is a perspective view of a cassette assembly according to an embodiment of the present invention with a comb inserted in the upper end of the cassette.
Figure 2:
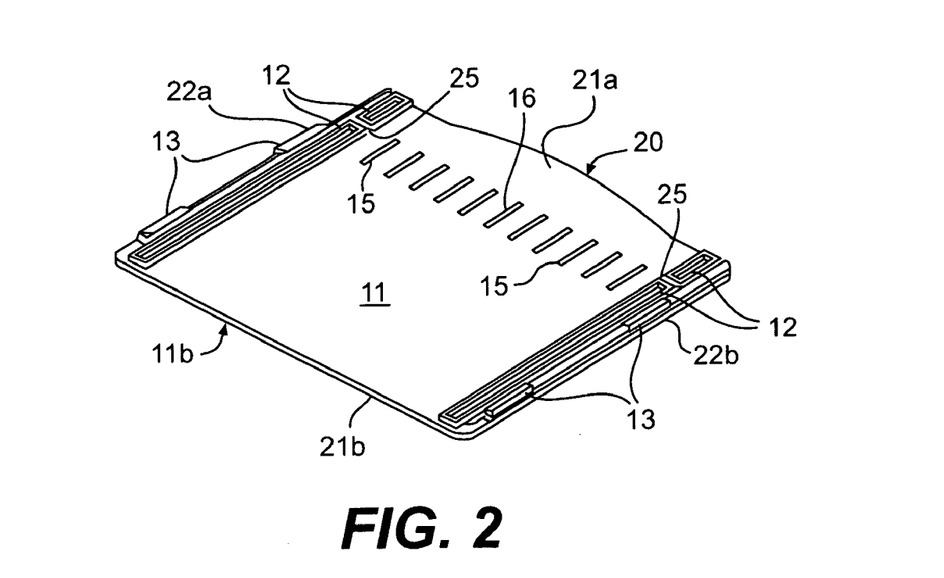
FIG. 2 is a perspective view of a first wall member of a cassette assembly according to the first aspect of the invention.
Figure 3:
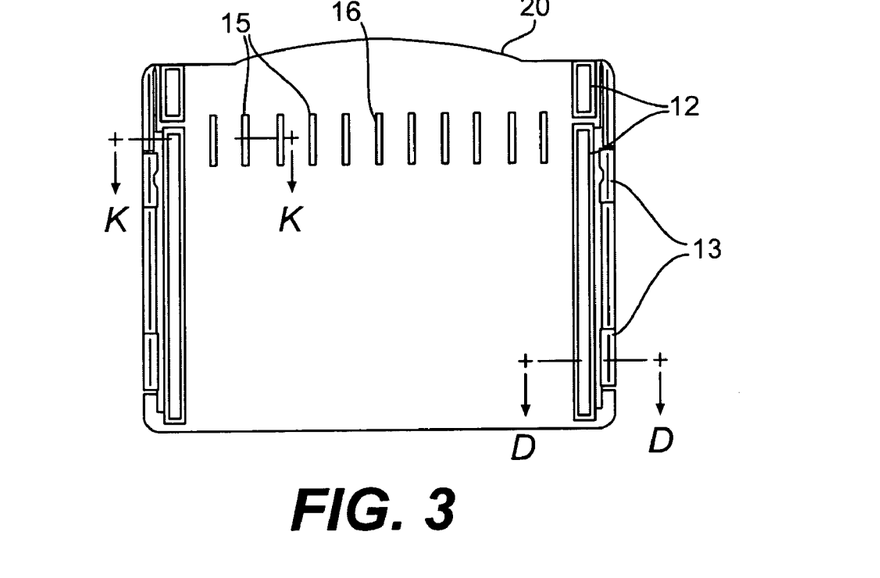
FIG. 3 is a plan view of the first wall member.
Figure 4:
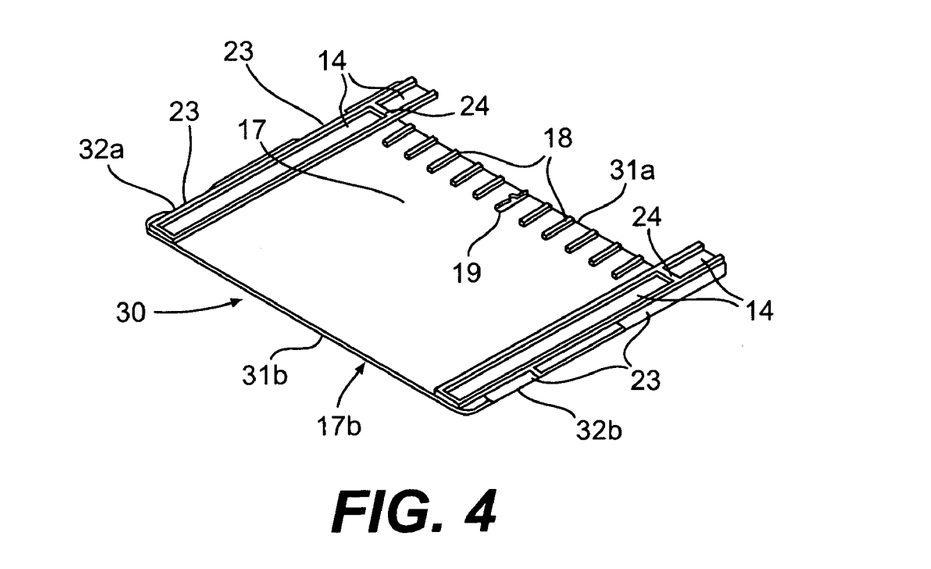
FIG. 4 is a perspective view a second wall member of a cassette assembly according to a first aspect of the invention.
Figure 5:
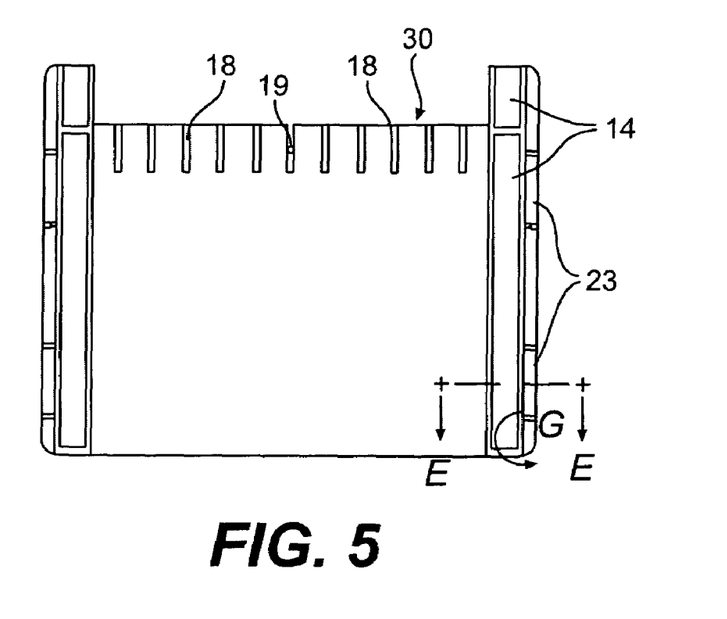
FIG. 5 is a plan view of the second wall member of a cassette.
Figure 6:
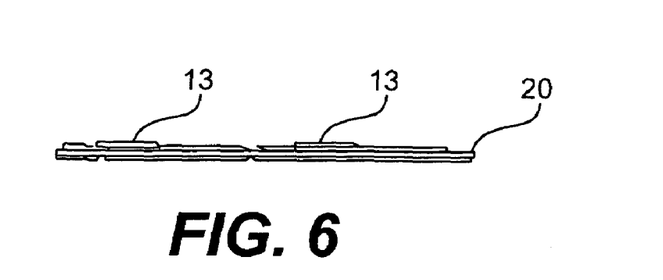
FIG. 6 is a side view of the first wall member shown in FIG. 2.
Figure 7:
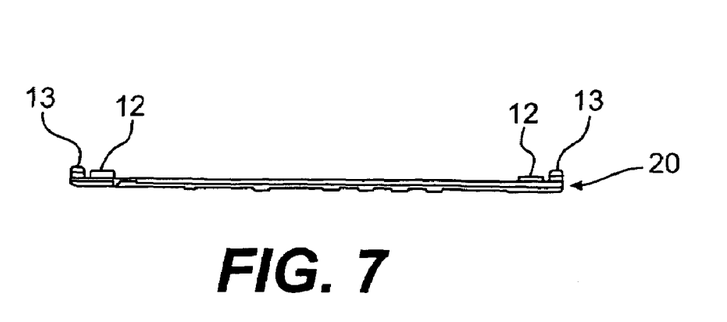
FIG. 7 is an end view of the first wall member shown in FIG. 3.
Figure 8:
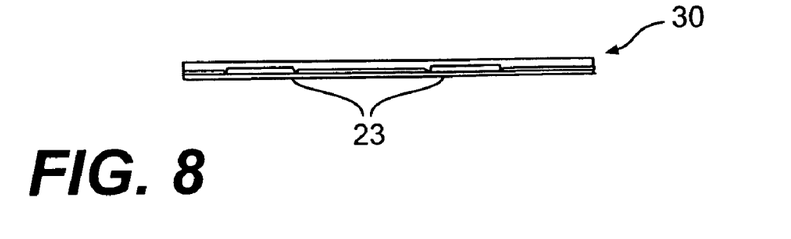
FIG. 8 is a side view of the second wall member shown in FIG. 4.
Figure 9:
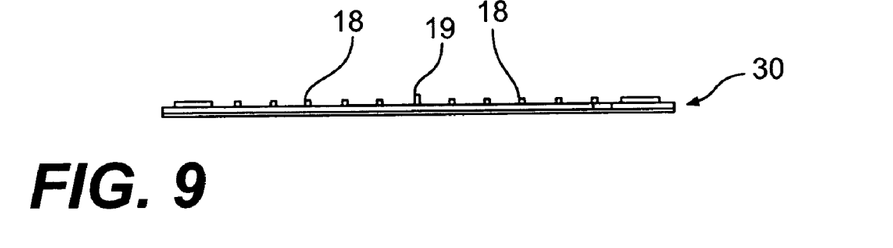
FIG. 9 is an end view of the second wall member shown in FIG. 5.

As shown in FIGS. 1 to 3, the electrophoresis cassette 10 is formed in two parts by injection molding or by other methods from a suitable synthetic plastics material. As shown in FIGS. 2, 3, 6, and 7, one part forms a first side wall 20 of the cassette having an inner surface 11 and an outer surface 11b, upper and lower ends 21a and 21b respectively, and two sides 22a and 22b. The first side wall is bounded on each side by spacer means comprising a pair of protruding ridges 12 located adjacent each lateral edge. The first side wall 20 also contains 2 pairs of male members 13 positioned at or near the lateral edges.

As shown in FIGS. 4, 5, 8, and 9, the other part forms a second side wall 30 of the cassette having an inner surface 17 and an outer surface 17b, upper and lower ends 31a and 31b respectively, and two sides 32a and 32b. The second side wall is bounded on each side by a pair of spaced apart projections 14. When the first and second side walls are in locked engagement, the ridges 12 and 14 interdigitate to form a seal along each side of the cassette 10. This seal inhibits leakage therethrough of the gel forming liquid during setting of the gel or the electrical current during electrophoresis. The second side wall 30 also contains 2 pairs of indented sections 23 which form another part of the locking means. These indented sections 23 are located on the lateral edges of the side wall 30.

The ridges 12 and 14 are dimensioned so that, when the side walls 20, 30 are in locked engagement, a gel receiving space (not shown) of desired thickness is defined between the side walls 20, 30 which lie in substantially parallel planes.

In order to assist in the positioning of the two parts of the cassette 10, locating lugs 24 are positioned across the ridges 14. There are corresponding gaps 25 in the ridges of the first side wall, adapted to receive said lugs 24. The lugs 24 and gaps 25 are positioned relative to or above the bottom of wells formed in the gel so as to ensure that, during casting of the gel in the cassette 10, the gel (prior to setting) does not leak through any space formed between the lugs 24 and the gaps 25. These lugs 24 and gaps 25 are particularly helpful in vertically aligning the two wall members.

The inner face 11 of the first side wall 20 has a series of short parallel grooves 15 formed therein. One of these grooves has a small substantially circular mouth 16 extending deeper into the groove. The inner face 17 of the second side wall 30 has a series of short parallel ribs 18 formed thereon. Each rib 18 has a base diameter of approximately 0.8 mm. The ribs 18 are aligned in a row evenly spaced apart and closely adjacent to an upper end of the first side wall 20.

One of the ribs has a small substantially circular stud 19 projecting up from the rib.

Figure 16:
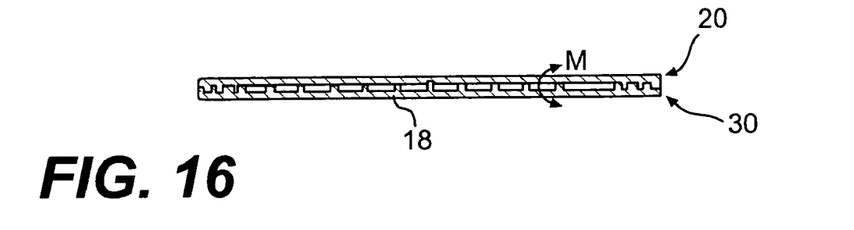
FIG. 16 is a top cross-sectional view of the cassette of FIG. 1.
Figure 17:
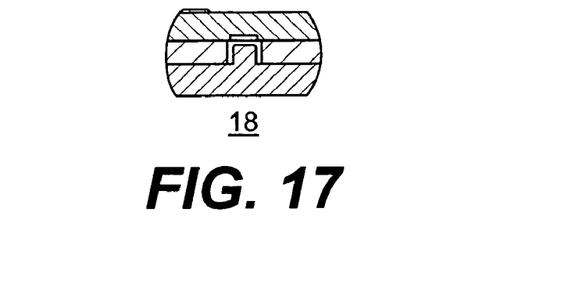
FIG. 17 is a partial top cross-sectional view of the cassette of FIG. 1.

As shown in FIGS. 16 and 17, when the two parts of the cassette are engaged, the ribs 18 and grooves 15 are in alignment. The ribs 18 may extend fully across the gel receiving space so that the ends of the ribs 18 are received within the grooves 15. In this case, the ribs 18 may help to maintain a constant distance between the inner faces 11, 17 of the side walls.

However, it is not necessary that the ribs 18 are received within the grooves 15. As shown in FIG. 17, the top of each rib 18 is separated from each corresponding groove 15 by a small gap. When the two parts are engaged, the stud 19 is received within the mouth 16 and is held in place, preferably by a snap-fit. This serves to maintain a constant distance between the inner faces 11, 21.

Figure 10:
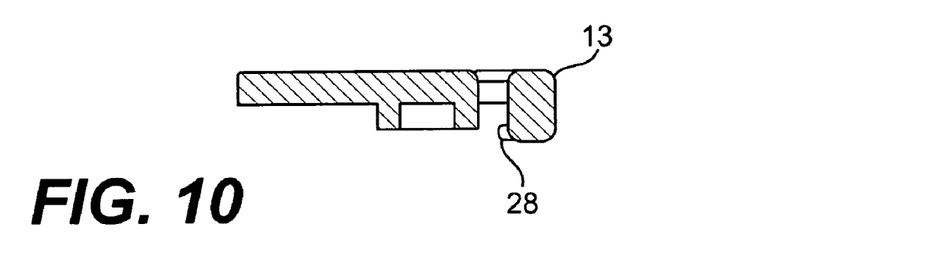
FIG. 10 is a cross-sectional view of a lateral side of the first wall member shown in FIG. 7.
Figure 11:
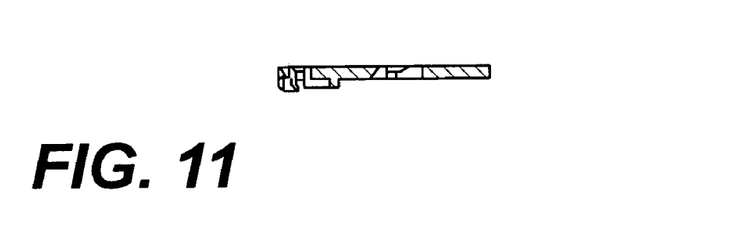
FIG. 11 is another cross-sectional view of a lateral side of the first wall member shown in FIG. 7.
Figure 12:
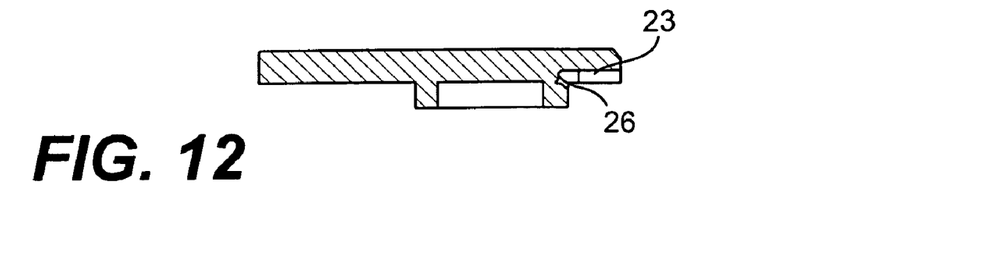
FIG. 12 is a cross-sectional view of a lateral side of the second wall member shown in FIG. 9.
Figure 13:
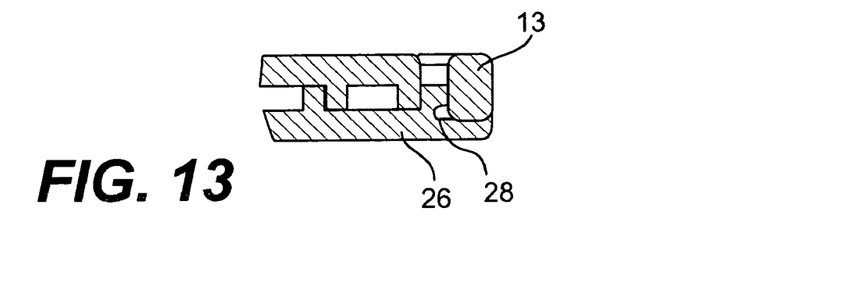
FIG. 13 is a cross-sectional view showing engagement of the lateral sides of the first and second wall members shown in FIGS. 10 and 12.
Figure 14:
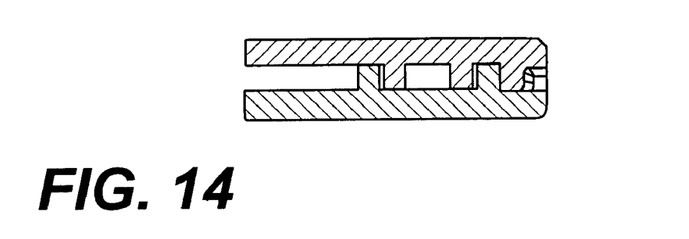
FIG. 14 is a cross-sectional view showing engagement of lateral sides of first and second wall members of an alternative embodiment of this invention.
Figure 15:
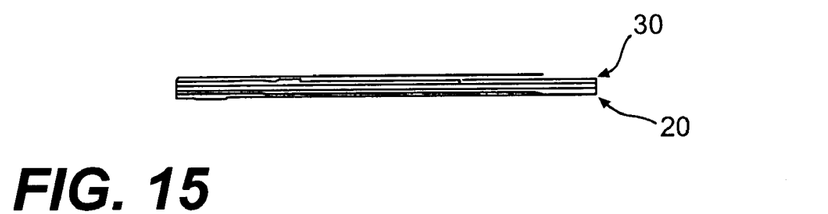
FIG. 15 is a side view of the cassette when the first and second wall members are engaged.

Locked engagement of the two parts is effected by the locking means consisting of the 2 pairs of male members 13 and the 2 pairs of indented sections 23. The male members 13 have a substantially L-shaped cross-section having a clawed end 28 (as more particularly shown in FIGS. 10 and 11). Each indented section 23 has a furrow 26 extending along the section (as more particularly shown in FIG. 12). The clawed end 28 and the furrow 26 are dimensioned so that, when the two parts are locked together, the clawed end 28 and the furrow 26 inter-engage in a snap fit. FIGS. 13 and 14 show the inter-engagement of the clawed end 28 and the furrow 26. The locked engagement of the two wall members is shown in FIG. 15.

Figure 21:
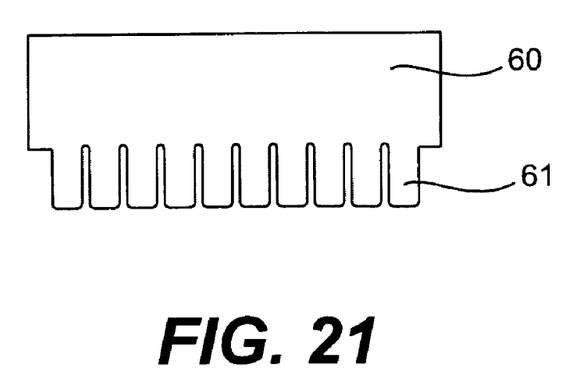
FIG. 21 is a plan view of a comb for use in conjunction with the cassette of FIG. 1.

To form a gel in the cassette, a comb 60 with a plurality of spaced apart teeth 61 (as shown in FIG. 21) is inserted into one end of the cassette. The teeth 61 are so dimensioned that they interdigitate with the ribs 18 but are at all times closely spaced therefrom. The teeth 61 prevent gel (which has not yet set) from escaping up through the channels between the ribs 18. After the gel has formed in the gel-receiving space, the cassette can be used.

When the comb 60 is withdrawn from the cassette, there will be a plurality of wells formed in the gel. The wells are separated by tongues of gel formed when gel forming liquid enters between the adjacent ribs and sets. Each tongue will extend to and surround one of the ribs. The ribs will serve to support the tongue of gel without substantially disturbing the flow of electric current through the cassette during use.

In one embodiment, there are many ribs, either on one or both of the side walls which extend inwardly into the gel-receiving space, to partly or fully span the gel-receiving space. Alternatively, ribs are suitably located on the two side walls and the ribs alternate across the width of the cassette. Rather than being conical, the ribs are suitably cylindrical, diamond, or in the form of rectangular or triangular prisms, or other geometrical forms. There are suitably one or more projections aligned along the length of each tongue. In another embodiment each tongue may surround one or more laterally spaced apart projections.

In alternative embodiment, the cassette is further comprised of an electrophoresis gel material within the interior of the cassette, wherein the gel comprises at least two gel fingers, separated from each other, and located proximate to the upper end of the gel, at least two wells located above the at least two gel fingers, wherein one of the wells is larger than the other well; and a removable plug located in the smaller of the wells. Preferably, the gel fingers are separated by a narrow wall or finger, wherein the wall or finger is at least partially formed by the gel material.

By providing a partially solid finger, it is not necessary to provide a two-well comb to support the wells during transportation and storage. Instead, a small removable plug is inserted into the small well to prevent it from filling up during the step where the first-dimension gel is embedded. After the first-dimension gel has been embedded into position and the embedding solution has set or polymerized, the plug can be removed and discarded and the small well can be loaded with protein. This invention allows the operator to use the product immediately and with much greater convenience than with existing pre-cast gels.

Typically, the large well is approximately 7 cm in length.

The material forming a gel in the apparatus may be any medium that can be used to separate proteins, an example is crosslinked polyacrylamide gel.

The cassette is made from any suitable material. Typical suitable plastic materials include, but are not limited to, thermoplastics, such as polymethyl methacrylate, styrene acrylonitrile, polycarbonate, polyethylene naphthalate, polyvinyl chloride, polyvinylidene chloride or polyethylene tetra-phthalate, or a composite of any of these. Alternatively, the cassette material is glass or a combination of glass and plastic.

The plug is made from any suitable material. Typical suitable plastic materials include, but are not limited to, thermoplastics, such as polymethyl methacrylate, styrene acrylonitrile, polycarbonate, polyethylene naphthalate, polyvinyl chloride, polyvinylidene chloride or polyethylene tetra-phthalate, or a composite of any of these. Alternatively, the plug material is suitably glass or a combination of glass and plastic.

The material used for the cassette or the plug is optionally coated, for example, with a barrier layer which can be either hydrophilic or hydrophobic.

Figure 18:
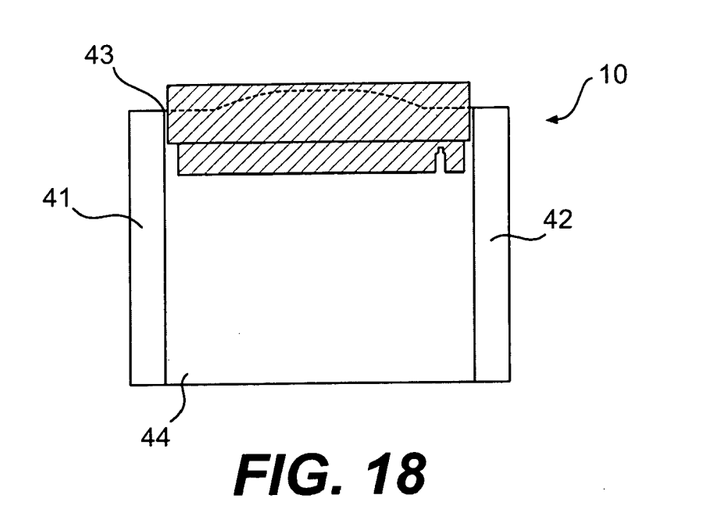
FIG. 18 shows a gel cassette post-manufacture after the slab has been cast, included a large comb used to define the wells during manufacture.
Figure 19:
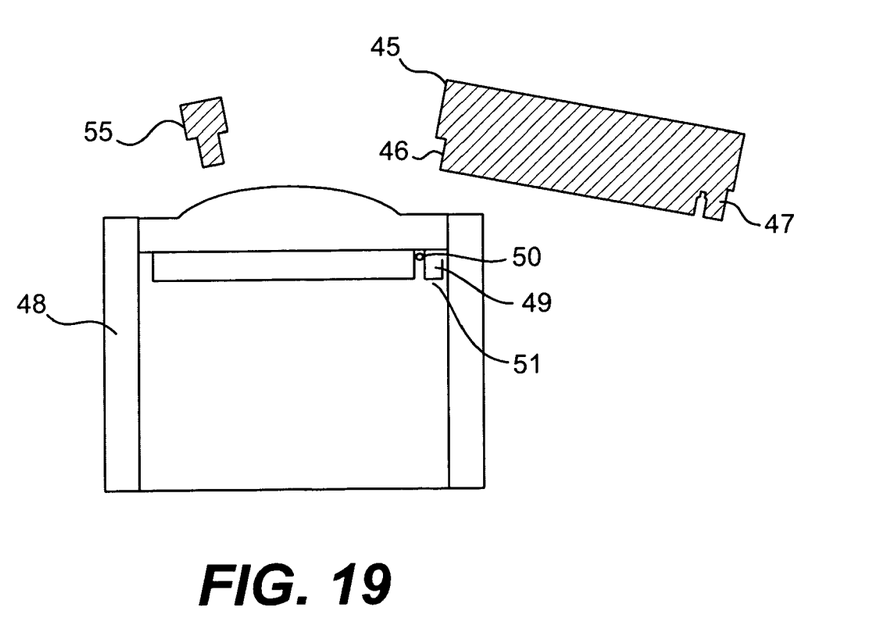
FIG. 19 shows the cassette after the large comb has been removed and the plug is ready to be inserted.
Figure 20:
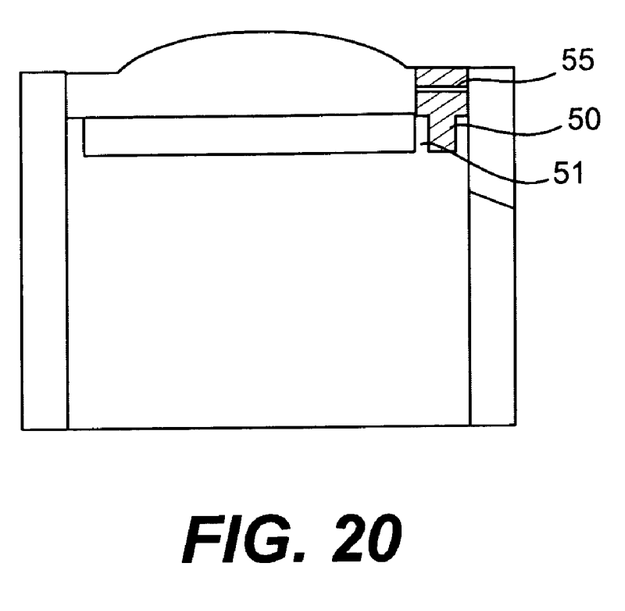
FIG. 20 shows the cassette with a plug protecting the small well and the large well exposed.

FIGS. 18, 19 and 20 show such alternative embodiment of the cassette of this invention. A gel cassette 10 is shown, comprising two parts with substantially planar walls 20, 30 having two sides 41, 42 and upper and lower ends 43, 44 arranged in a parallel spaced apart array to form a gel receiving space therebetween. A slab gel is located in the space. The slab gel is formed from a gel forming material such as acrylamide or agarose which is allowed to polymerase or set while a two-well comb 45 is inserted into the upper end 43 of the cassette. The comb 45 defines a large projection 46 and a relatively smaller projection 47 which form a relatively larger well 48 and a relatively smaller well 49 in the gel slab, respectively. The larger well 48 is typically five to twenty times longer than the small well 49. As can be seen, the two wells are separated by a stud 50 (made of plastic) and by a finger 51 of the gel (which is part of the cassette). The plastic stud 50 extends from one plate of the cassette towards the other plate and also provides a locating means for locating the comb 45 as the two projections 46, 47 locate either side of it during the gel forming stage.

Once the gel has polymerized or set, the two-well comb 45 is removed leaving the large well 48 and the small well 49. A plug 55 is placed in the small well and the cassette is now ready for shipping, storage or use. The partially solid finger 51 is sufficiently self-supporting to obviate the need to ship or store the cassette with the two-well comb 51 included.

In another embodiment, the cassette is further comprised of positioning means adapted to position a removable buffer chamber on the upper end of the cassette; and a removable buffer chamber adapted to be positioned on the upper end of the cassette.

Preferably, the locating means is formed as extensions, prongs or arms on each lateral side of the cassette extending above the upper end of the cassette. The chamber preferably has corresponding receiving portions (such as a channeled section) on outer surfaces of end walls to engage with the extensions, prongs or arms.

Preferably, the buffer chamber has side walls and end walls forming a buffer-receiving chamber, an open upper end and a lower end having a cavity or slit positioned therein adapted to be sealably located on the upper end of the cassette.

The buffer chamber is preferably substantially symmetrical making it easier to load the first dimension strip onto the top of the gel. Again, as it is useful that the cassette be easily disassembled easily, the buffer chamber should be able to be removed from the rest of the cassette. This is achieved through attaching the chamber "prongs" to the sides of the cassette assembly. A good seal between the chamber and the rest of the cassette is achieved through applying an elastomeric seal to either of the components.

Having an integrated buffer chamber which extends outwards from both sides of the cassette, allows convenient removal of the chamber ensuring ease of opening of the cassette and reduced risk of damaging the gel. In addition, a removal chamber makes the gel pouring process easier and more reliable.

Figure 22:
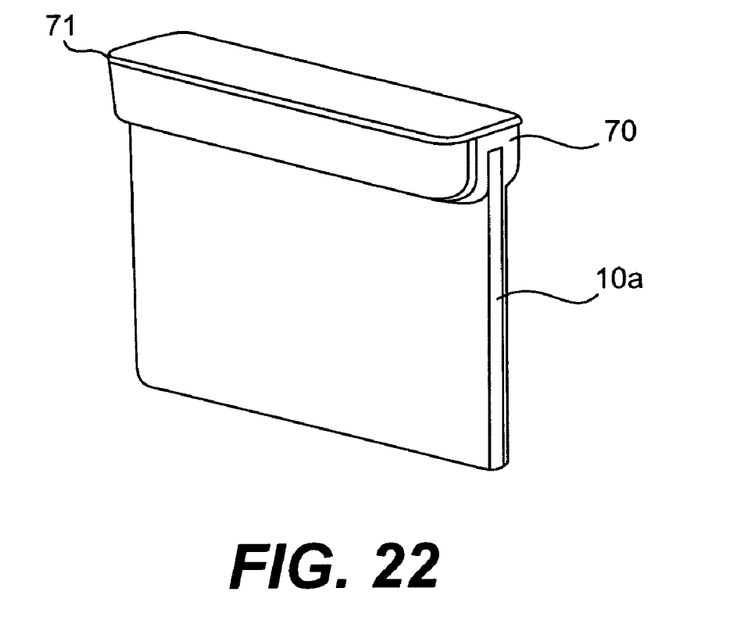
FIG. 22 is a perspective view of a cassette assembly according to an embodiment of the present invention with a buffer chamber attached thereto.
Figure 23:
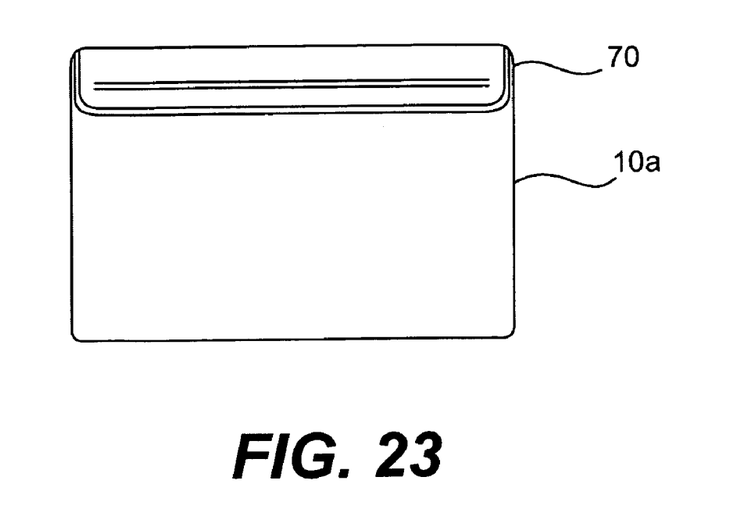
FIG. 23 is a plan view of the cassette assembly shown in FIG. 22.
Figure 24:
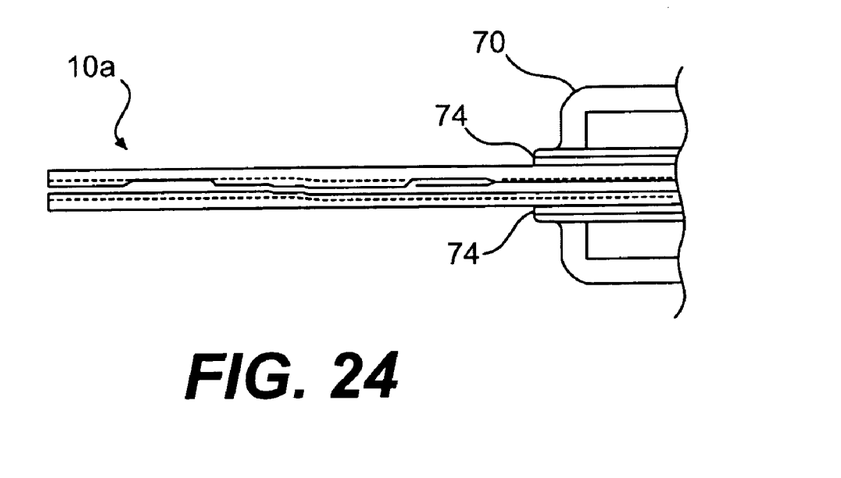
FIG. 24 is a side view of the cassette assembly shown in FIG. 22.

FIGS. 22, 23 and 24 show an electrophoresis cassette 10a having an elongated buffer chamber 70 connected to an upper portion of the cassette 10a. The buffer chamber 70 has an open trough 71 which, in use, receives and holds an electro-buffer material.

Figure 25:
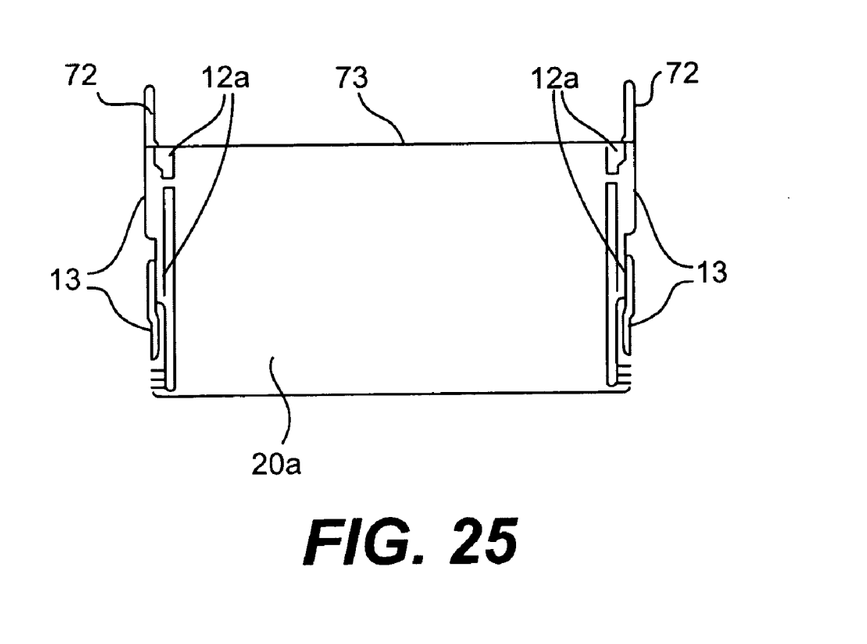
FIG. 25 is a plan view of a first wall member of the cassette assembly shown in FIG. 22.

The first wall member shown in FIG. 25 contains a first side wall 20a which is bounded on each side by spacer means being a pair of protruding ridges 12a located adjacent each lateral edge. The first side wall 20a also contains two pairs of male members 13 positioned at or near the lateral edges.

The first side wall 20a also contains two parallel arms 72 extending from the upper end of the first side wall 20a in alignment with the lateral edges.

Figure 26:
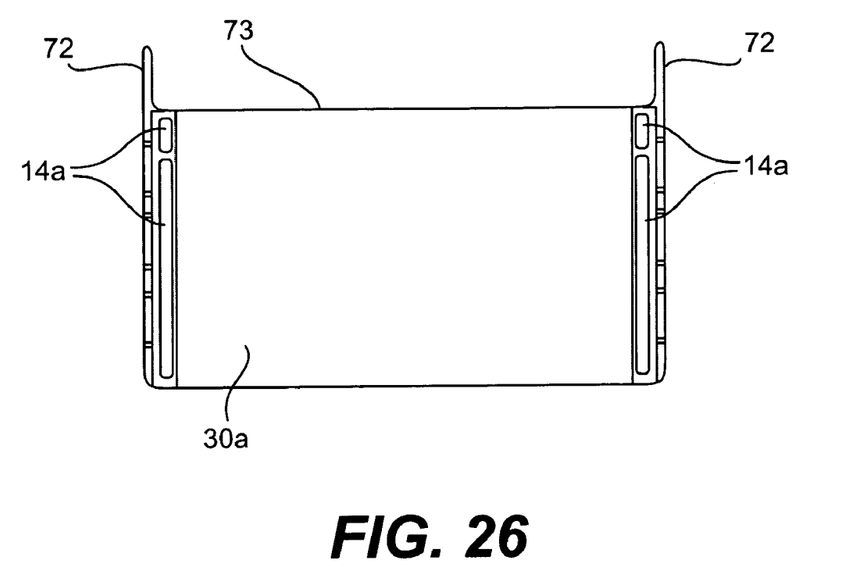
FIG. 26 is a plan view of a second wall member of the cassette assembly shown in FIG. 22.

The second wall member shown in FIG. 26 has a second side wall 30a. This second side wall 30a is bounded on each side by a pair of spaced apart projections, each of which encloses channels 14a.

Figure 27:
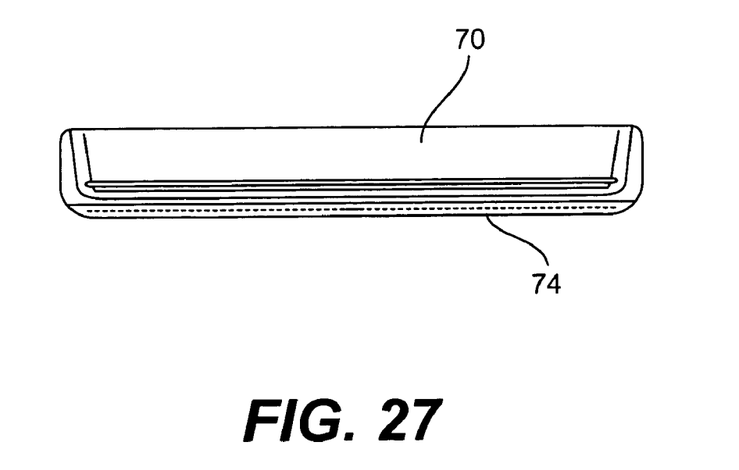
FIG. 27 is a plan view of the buffer chamber shown in FIG. 22.
Figure 28:
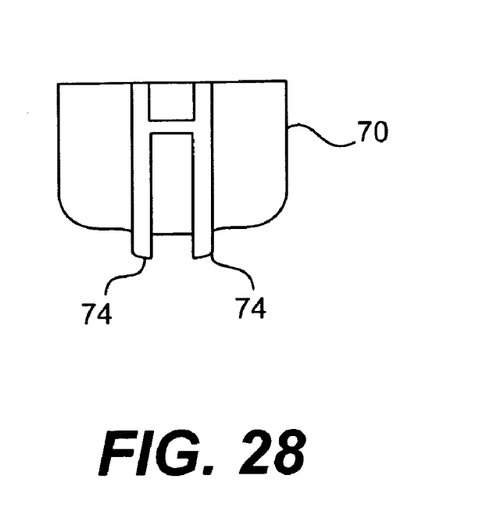
FIG. 28 is a side view of the buffer chamber shown in FIG. 27.

The second side wall 30a also has parallel arms 72 which are substantially the same as the parallel arms described above in respect of first side wall 20a. When the first and second wall members are in locked engagement, the parallel arms 72 and the top edge of the side walls 20a, 30a define a recess 73 into which is placed the buffer chamber 70. The buffer chamber contains a pair of parallel external ridges 74 which extend down each side and along the base of the buffer chamber 70. The buffer chamber 70 is positioned on top of the engaged first and second wall members by inserting the chamber 70 into the recess 73 so that inside surfaces of the ridges 74 abut external surfaces of the parallel arm 72 and the top edge of the two wall members (as more particularly shown in FIGS. 24, 27, and 28).

Figure 29:
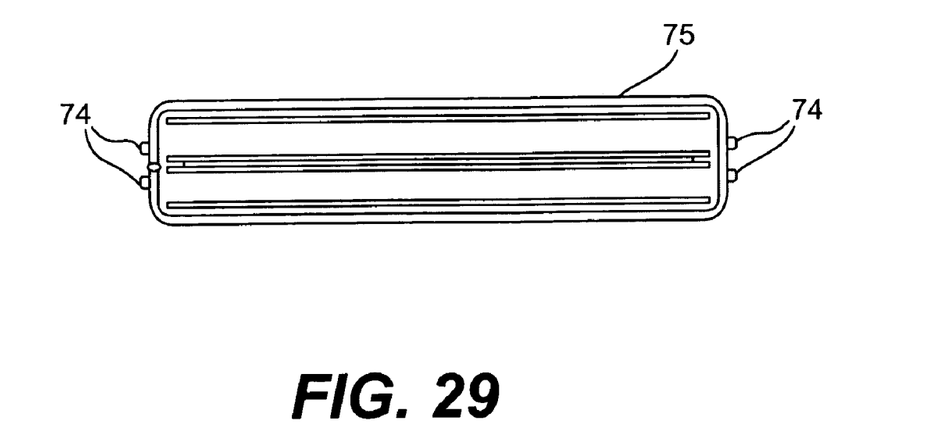
FIG. 29 is a top view of the buffer chamber shown in FIG. 27.

As shown in FIG. 29, the buffer chamber 70 has an elongated slit 75 extending along the base of the chamber. The elongated slit 75 enables a communication to occur between the buffer chamber 70 and the electrophoretic gel in the gel-receiving space.

In use, a first dimension gel is placed in the large well after a first dimension separation has been carried out in the gel. The first-dimension gel is then connected to a second-dimension gel typically using a polymer solvated in conducting material, such as agarose. Once the first-dimension gel and the second-dimension gel are joined and the embedding solution is set or polymerized, the small plug can be removed. Protein may be placed in the small well 30 for comparison with the movement of the proteins in the first-dimension gel as they travel down through the slab gel under the influence of an electric field.

In order to assist or improve the adhesion of the gel to the cassette, a transparent inorganic oxide film is deposited at least upon one of the surfaces of the cassette components forming the gel receiving space. It has been found that such films improve the adhesion of the gel to the components of the cassette by mimicking the surface characteristics of glass. The transparent inorganic oxide film is formed of silicon, aluminum, zircon or mixtures thereof.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive. Other features and aspects of this invention will be appreciated by those skilled in the art upon reading and comprehending this disclosure. Such features, aspects, and expected variations and modifications of the reported results and examples are clearly within the scope of the invention where the invention is limited solely by the scope of the following claims.

What is claimed is:

1. A method for preparing a pre-cast electrophoresis gel comprising:
   inserting at least one spacer into the top of a cassette for electrophoresis gels, the cassette comprising:
   a first planar wall member having inner and outer surfaces, top and bottom edges, and bottom edges and lateral edges;
   a second planar wall member having inner and outer surfaces, top and back edges, and lateral edges, wherein the first and second wall members are oriented generally parallel to each other and such that the inner wall of the first wall member is proximate to the inner wall of the second wall member;
   spacing means disposed between the inner walls of the first and second wall members and adapted to provide a space for an electrophoresis gel between the inner walls of the first and second wall members, wherein the cassette has an interior which is defined by the space between the first wall member and the second wall member; and
   locking means adapted to prevent locking engagement of the first and second wall members unless the inner surface of the first wall member and the inner surface of the second wall member are substantially parallel to each other and are separated by a predetermined distance and, when the first and second wall members are in locked engagement, to substantially prevent any movement of the wall members away from such locked engagement;
   wherein the spacer comprises a protrusion projecting from the side of the spacer proximate the interior of the cassette, wherein such protrusion defines two wells within the interior of the cassette, and wherein one of the wells is larger than the other well;
   providing a gel-forming material into the interior of the cassette;
   allowing the gel-forming material to form a gel within the interior of the cassette;
   removing the spacer from the cassette; and
   inserting a removable plug in the smaller well.

2. A cassette for holding a vertical electrophoretic gel for use in vertical gel electrophoresis comprising:
   first and second substantially planar vertical wall members;
   spacer means adapted to position the first and second wall members in opposed orientation so as to define between opposed inner faces of the wall members a gel-receiving space having open upper and lower ends and closed lateral sides, wherein the spacer means includes at least one primary spacing element located on an inner face and adjacent to each lateral edge of the wall member, wherein the primary spacing element includes ridges on one wall member and corresponding channels on the other wall member, and wherein the ridges and channels are adapted so that the ridges are receivable within the channels; and locking means, including at least one male member projecting from each side of one of the wall members and at least one complementary receiving member adjacent each side of the other wall member adapted to receive said male members, wherein said corresponding male members and receiving members are adapted not to effect locked engagement of the first and second wall members unless opposed inner faces of said wall members lie in parallel planes separated by a predetermined distance, wherein the male members and the receiving members are adapted to effect engagement by a snap-fit.

3. The cassette according to claim 2, wherein the locking means includes two male members projecting from each side of one of the wall members and two complementary receiving members adjacent each side of the other wall member.

4. The cassette according to claim 2, wherein each male member is an L-shaped member projecting from at or near each lateral edge of one of the wall members and each receiving member is a complementary ridge, indent or surface of the other wall member adapted so that a portion of each L-shaped member clamps over each complementary ridge, indent or surface of the other wall member.

5. The cassette according to claim 4 wherein the male members are integrally formed parts of the wall members.

6. The cassette according to claim 2, wherein the primary spacing elements are adapted to effect closure of the lateral sides of the gel-receiving space.

7. The cassette according to claim 6, wherein the primary spacing elements consist of cooperating ridges and channels extending along substantially the entire length of the wall members adjacent said lateral edges.

8. The cassette according to claim 2, wherein the spacer means further includes one or more secondary spacing elements located intermediate the lateral edges.

9. The cassette according to claim 8, wherein the one or more secondary spacing elements are adapted to maintain the predetermined distance between the opposed inner faces.

10. The cassette according to claim 9, wherein the one or more secondary spacing elements are positioned new the upper end of the gel-receiving space.

11. The cassette according to claim 8, wherein each secondary spacing element consists of a boss or knob on one inner face and a complementary mouth on the opposed inner face adapted to receive the boss or knob.

12. The cassette according to claim 2, wherein the inner face of one of the wall members includes one or more of short longitudinal ribs adjacent to an upper end of the wall member.

13. The cassette according to claim 12, wherein the one or more short ribs are adapted so that, when the first and second walls members are engaged, the short ribs define a plurality of parallel channels suitable for receiving a well-forming cone or spacer.

14. The cassette according to claim 13, wherein the one or more short ribs are adapted so as to extend fully between the opposed inner faces of the first and second wall members when the members are in locked engagement.

15. The cassette according to claim 13, wherein the one or more short ribs are adapted so as to extend only partly between said inner faces when in locked engagement, so as to define a channelled gel-receiving cavity.

16. The cassette according to claim 12, wherein the one or more short ribs are separated by substantially equal distances.

17. The cassette according to claim 12, wherein the cassette is adapted so that, when filled with gel, the short ribs cause gel fingers to be formed within the gel-receiving cavity and cause sample-receiving wells to be formed on top of the gel fingers.

18. The cassette according to claim 2, further comprising:
locating means for positioning a removable buffer chamber on the upper end of the cassette; and
a removable elongated buffer chamber adapted to be positioned on the upper end of the cassette.

19. The cassette according to claim 18, wherein the locating means is formed as extensions or prongs on each lateral side of the cassette extending above the upper end of the cassette.

20. The cassette according to claim 19, wherein the buffer chamber has side walls and end walls forming a buffer receiving chamber, an open upper end and a lower closed end having a cavity positioned therein adapted to be sealably located on the upper end of the cassette.

21. The cassette according to claim 20, wherein the buffer chamber has corresponding receiving portions on outer surfaces of the end walls to engage with the extensions or prongs.

22. The cassette according to claim 2 further comprising:
gel material formed in the gel-receiving space defining at least two wells in the upper end of the gel, one of the two wells being relatively larger and the other one well being relatively smaller;
a narrow wall or finger separating the relatively smaller well from the larger well wherein the wall or finger is at least partially defined by the gel material forming the slab; and
a removable plug located in the smaller well.

23. A method for making a pre-cast electrophoresis gel for vertical gel electrophoresis comprising:
providing a vertical cassette according to claim 2;
placing a comb or at least one spacer in the top of the cassette;
pouring a gel-forming material into the cassette;
allowing the gel forming material to polymerise or set; and
removing the comb or spacer.

24. A method for making a pre-cast electrophoresis gel for 2-D vertical gel electrophoresis comprising:
providing a vertical cassette according to claim 2;
placing a comb having two space-defining projections in the top of the cassette, wherein one projection is relatively wider than the other projection;
pouring a gel-forming material into the cassette;
allowing the gel forming material to polymerise or set;
removing the comb or spacer to form a relatively wider well and a relatively smaller well; and
placing a removable plug in the relatively smaller well.

25. A method for making a pre-cast electrophoresis gel for 2-D vertical gel electrophoresis comprising:
providing a vertical cassette comprising first and second substantially planar vertical wall members; spacer means adapted to position the first and second wall members in opposed orientation so as to define between opposed inner faces of the wall members a gel-receiving space having open upper and lower ends and closed lateral sides; and locking means, including at least one male member projecting from each side of one of the wall members and at least one complementary receiving member adjacent each side of the other wall member adapted to receive said male members, wherein said corresponding male members and receiving members are adapted not to effect locked engagement of the first and second wall members unless opposed inner faces of said wall members lie in parallel planes separated by a predetermined distance, wherein the male members and the receiving members are adapted to effect engagement by a snap-fit;
placing a comb having two space-defining projections in the top of the cassette, wherein one projection is relatively wider than the other projection;
pouring a gel-forming material into the cassette;
allowing the gel forming material to polymerise or set;
removing the comb or spacer to form a relatively wider well and a relatively smaller well; and
placing a removable plug in the relatively smaller well.

26. A method for preparing a pre-cast electrophoresis gel for vertical gel electrophoresis comprising:
inserting at least one spacer into the top of a cassette for vertical electrophoresis gels, the cassette comprising:
a first vertical planar wall member having inner and outer surfaces, top and bottom edges, and bottom edges and lateral edges;
a second vertical planar wall member having inner and outer surfaces, top and back edges, and lateral edges, wherein the first and second wall members are oriented generally parallel to each other and such that the inner wall of the first wall member is proximate to the inner wall of the second wall member;
spacing means disposed between the inner walls of the first and second wall members and adapted to provide a space for an electrophoresis gel between the inner walls of the first and second wall members, wherein the cassette has an interior which is defined by the space between the first wall member and the second wall member; and
locking means adapted to prevent locking engagement of the first and second wall members unless the inner surface of the first wall member and the inner surface of the second wall member are substantially parallel to each other and are separated by a predetermined distance and, when the first and second wall members are in locked engagement, to substantially prevent any movement of the wall members away from such locked engagement;
wherein the spacer comprises a protrusion projecting from the side of the spacer proximate the interior of the cassette, wherein such protrusion defines two wells within the interior of the cassette, and wherein one of the wells is larger than the other well;
providing a gel-forming material into the interior of the cassette;
allowing the gel-forming material to form a gel within the interior of the cassette;
removing the spacer from the cassette; and
inserting a removable plug in the smaller well.

* * * * *